(12) United States Patent
Kimball

(10) Patent No.: US 11,395,770 B2
(45) Date of Patent: Jul. 26, 2022

(54) TAMPON PRESS JAWS

(71) Applicant: JOHNSON & JOHNSON GMBH, Neuss (DE)

(72) Inventor: David L. Kimball, Flemington, NJ (US)

(73) Assignee: Johnson & Johnson GmbH, Neuss (DE)

( * ) Notice: Subject to any disclaimer, the term of this patent is extended or adjusted under 35 U.S.C. 154(b) by 413 days.

(21) Appl. No.: 16/635,669

(22) PCT Filed: May 31, 2018

(86) PCT No.: PCT/IB2018/053922
§ 371 (c)(1),
(2) Date: Jan. 31, 2020

(87) PCT Pub. No.: WO2018/220587
PCT Pub. Date: Dec. 6, 2018

(65) Prior Publication Data
US 2021/0007904 A1    Jan. 14, 2021

Related U.S. Application Data

(60) Provisional application No. 62/513,761, filed on Jun. 1, 2017.

(51) Int. Cl.
*A61F 13/20* (2006.01)
(52) U.S. Cl.
CPC ...... *A61F 13/2088* (2013.01); *A61F 13/2091* (2013.01)

(58) Field of Classification Search
CPC .............. A61F 13/2088; A61F 13/2091; A61F 13/2085; A61F 13/2082; A61F 13/2054;
(Continued)

(56) References Cited

U.S. PATENT DOCUMENTS 2,263,909 A    11/1941    Webb
2,425,004 A     8/1947    Rabell
(Continued)

FOREIGN PATENT DOCUMENTS

DE    40502965-0001    10/2005
DE    40502965-0002    10/2005
(Continued)

OTHER PUBLICATIONS

International search report and written opinion dated Sep. 12, 2018, for international application PCT/IB2018/053922.
(Continued)

*Primary Examiner* — Amy Vanatta

(57) ABSTRACT

An apparatus for manufacturing an intravaginal tampon for feminine hygiene includes a tampon press having a plurality of elongate press dies disposed about central press axis to form a press cavity and a cylindrical carrier having a diameter less than that of the predetermined finished diameter. The elongate press dies include a plurality of longitudinal penetrating dies, each having a pressing face notch disposed proximate a first end thereof and an end notch disposed on an edge perpendicular to the pressing face at the opposite second end thereof that cooperate with corresponding notches in an adjacent penetrating die.

5 Claims, 16 Drawing Sheets

(58) Field of Classification Search
CPC ............ A61F 13/2094; A61F 13/15707; A61F 2013/15715; A61F 13/15764
USPC .......................................................... 28/118
See application file for complete search history.

(56) References Cited

U.S. PATENT DOCUMENTS

| | | | |
|---|---|---|---|
| 2,798,260 | A | 7/1957 | Friedrich et al. |
| 3,422,496 | A | 1/1969 | Wolff et al. |
| 3,596,328 | A | 8/1971 | Voss |
| 3,683,915 | A | 8/1972 | Voss |
| 4,109,354 | A | 8/1978 | Ronc |
| 4,816,100 | A | 3/1989 | Friese |
| 4,951,368 | A | 8/1990 | Heinen |
| 5,458,835 | A | 10/1995 | Wilkes et al. |
| 5,592,725 | A | 1/1997 | Brinker |
| 5,813,102 | A | 9/1998 | Leutwyler et al. |
| 5,832,576 | A * | 11/1998 | Leutwyler ............ A61F 13/2051 28/118 |
| 5,909,884 | A | 6/1999 | Schwankhart |
| 6,310,269 | B1 | 10/2001 | Friese et al. |
| D477,075 | S | 7/2003 | Schoelling |
| D485,354 | S | 1/2004 | Carlin et al. |
| 6,758,839 | B2 | 7/2004 | Lochte et al. |
| 7,311,699 | B2 | 12/2007 | Carlin |
| 7,549,982 | B2 | 6/2009 | Carlin |
| 7,833,210 | B2 | 11/2010 | Schoelling |
| 7,845,055 | B1 | 12/2010 | Kimball et al. |
| D647,610 | S | 10/2011 | Smet |
| D647,611 | S | 10/2011 | Smet |
| D647,612 | S | 10/2011 | Smet |
| 8,029,485 | B2 | 10/2011 | Jensen |
| 8,153,582 | B2 | 4/2012 | Carlucci |
| 8,574,210 | B2 | 11/2013 | Van Ingelgem et al. |
| 8,747,378 | B2 | 6/2014 | Van Ingelgem et al. |
| 8,827,975 | B2 | 9/2014 | Kimball et al. |
| 8,834,439 | B2 | 9/2014 | Kimball et al. |
| 9,168,184 | B2 | 10/2015 | Kimball et al. |
| D804,655 | S | 12/2017 | Holliday et al. |
| 10,010,456 | B2 | 7/2018 | Kimball et al. |
| 10,010,457 | B2 | 7/2018 | Kimball et al. |
| 2002/0151859 | A1 | 10/2002 | Schoelling |
| 2005/0113785 | A1 | 5/2005 | Jensen |
| 2005/0193536 | A1 | 9/2005 | Ingelgem et al. |
| 2007/0083182 | A1 | 4/2007 | Schoelling |
| 2008/0200892 | A1 | 8/2008 | Van Ingelgem et al. |
| 2008/0254098 | A1 | 10/2008 | Ehrlich et al. |
| 2009/0024103 | A1 | 1/2009 | Van Ingelgem et al. |
| 2011/0092940 | A1 | 4/2011 | Fung et al. |
| 2011/0238028 | A1 | 9/2011 | Smet |
| 2012/0010587 | A1 | 1/2012 | Smet |
| 2012/0089111 | A1 | 4/2012 | Magnusson et al. |
| 2012/0137479 | A1 | 6/2012 | Rolli et al. |
| 2012/0187600 | A1 | 7/2012 | Graber |
| 2012/0238990 | A1 | 9/2012 | Jackson et al. |
| 2012/0283685 | A1 | 11/2012 | Amundson et al. |
| 2013/0110074 | A1 | 5/2013 | Smet et al. |
| 2014/0088539 | A1 | 3/2014 | Kimball et al. |
| 2014/0088540 | A1 | 3/2014 | Kimball et al. |
| 2014/0088541 | A1 | 3/2014 | Kimball et al. |
| 2014/0090218 | A1 | 4/2014 | Gehling et al. |
| 2014/0090219 | A1 | 4/2014 | Gehling et al. |
| 2014/0093604 | A1 | 4/2014 | Gehling et al. |
| 2015/0193536 | A1 | 7/2015 | Malik |
| 2016/0022507 | A1 | 1/2016 | Kimball et al. |
| 2016/0022508 | A1 | 1/2016 | Kimball et al. |
| 2017/0216102 | A1 * | 8/2017 | Hilt ..................... A61F 13/2037 |
| 2017/0231832 | A1 * | 8/2017 | Hilt ..................... A61F 13/2054 425/330 |
| 2019/0216655 | A1 * | 7/2019 | Gehling ............. A61F 13/2091 |

FOREIGN PATENT DOCUMENTS

| | | |
|---|---|---|
| DE | 40502965-0003 | 10/2005 |
| DE | 40502965-0004 | 10/2005 |
| DE | 40502965-0005 | 10/2005 |
| DE | 40502965-0006 | 10/2005 |
| DE | 40502965-0007 | 10/2005 |
| DE | 40502965-0008 | 10/2005 |
| DE | 40502965-0009 | 10/2005 |
| DE | 40502965-0010 | 10/2005 |
| EP | 422660 A | 4/1991 |
| EP | 611562 A | 8/1994 |
| EP | 1459720 A | 9/2004 |
| EP | 1459720 B | 9/2004 |
| EP | 1481656 A | 12/2004 |
| EP | 1547555 A | 6/2005 |
| EP | 1683503 A | 7/2006 |
| EP | 1983953 B | 10/2008 |
| EP | 2404584 A | 1/2012 |
| EP | 2712594 A | 4/2014 |
| EP | 2712596 A | 4/2014 |
| WO | WO 2007/088057 A | 8/2007 |
| WO | WO 2008/095937 A | 8/2008 |
| WO | WO 2008/135925 A | 11/2008 |
| WO | WO 2009/129910 A | 10/2009 |
| WO | WO 2010/069908 A | 1/2010 |
| WO | WO 2010/144061 A | 12/2010 |
| WO | WO 2011/000507 A | 1/2011 |
| WO | WO 2011/002357 A | 1/2011 |
| WO | WO 2012/004315 A | 1/2012 |
| WO | WO 2012/053986 A | 4/2012 |

OTHER PUBLICATIONS

A girl's guide to tampon use, posted at sheknows.com, posting date May 15, 2010, © sheknows.com, [online], [site visited Nov. 24, 2015]. Available from Internet, <URL: http://www.sheknows.com/health-and-wellness/articles/814191/a-girl-s-guide-to-tampon-use-1>.

* cited by examiner

TAMPON PRESS JAWS

CROSS-REFERENCE TO RELATED APPLICATIONS

This application is the national stage filing under 35 USC 371 of international application PCT/IB2018/053922 filed on May 31, 2018, which claims the benefit of U.S. provisional application 62/513,761 filed on Jun. 1, 2017.

FIELD OF THE INVENTION

The present invention relates to a manufacturing apparatus for an improved intravaginal tampon for feminine hygiene.

BACKGROUND OF THE INVENTION

Devices for intravaginally capturing and storing bodily fluid are commercially available and known in the literature. Intravaginal tampons for feminine hygiene are the most common example of such devices. Commercially available tampons are generally compressed cylindrical masses of absorbent fibers that may be contained by an absorbent or nonabsorbent cover layer.

The tampon is inserted into the human vagina and retained there for a time for the purpose of capturing and storing intravaginal bodily fluids, most commonly menstrual fluid. As intravaginal bodily fluid contacts the tampon, it should be absorbed and retained by the absorbent material of the tampon. After a time, the tampon and its retained fluid is removed and disposed, and if necessary, another tampon is inserted.

A drawback often encountered with commercially available tampons is the tendency toward premature failure, which may be defined as bodily fluid leakage from the vagina while the tampon is in place and before the tampon is completely saturated with the bodily fluid. The patent art typically describes a problem believed to occur that an unexpanded, compressed tampon is unable to immediately absorb fluid. Therefore, it presumes that premature leakage may occur when bodily fluid contacts a portion of the compressed tampon, and the fluid is not readily absorbed.

One way to prevent premature leakage from occurring is to provide designed pathways for fluid moving along the outer tampon surface. While this increase to the pathways may improve the fluid absorption, adding grooves during the manufacturing process can raise process issues. The prior art is replete with examples of attempts to incorporate grooves into tampons. Often new steps are added to an already complicated manufacturing process or the process is not fully described.

Friese et al., EP 0422660 B2, discloses an apparatus for producing a tampon with longitudinal grooves. The apparatus for making the tampon includes two groups of dies arranged in a plane perpendicular to the press axis. The first group of dies form press segments and the second group of dies form sliding plates. Each of the dies has press cutters projecting from the faces. The blank is pressed into a preform having a core with high compression and longitudinal ribs separated by grooves. The dies do not include a surface for forming shoulders.

Schoelling, US 2002-0151859 A1, discloses an apparatus for producing tampons having spirally shaped, pressed longitudinal grooves. The apparatus has press jaws of substantially equal dimensions which are arranged in a star formation with respect to the press axis. The jaws can be moved synchronously between open and closed positions. Each press jaw has a stepped pressing surface including a pressing blade and a pressing shoulder. The area of the pressing shoulder is great than the area of the pressing blade. The pressing blade and pressing shoulder can extend over a circumferential angle α of between 80 to 150° in the closed or pressing position. The press jaws are slightly retracted to give clearance when the preform is ejected from the press.

Van Ingelgem et al., EP 1547555 B1 purports to disclose an apparatus for manufacturing tampons with at least three press jaws, each press jaw having a penetrating segment for penetrating the absorbent material and pressing shoulder. The median of the penetrating segment diverges from the radius of that penetrating segment when in the press. The median of the penetrating segment is the straight line drawn in a cross section of the penetrating segment, through its tip and the midpoint of its base. One press jaw may comprise either a penetrating segment or a pressing shoulder, or a combination of one penetrating segment and pressing shoulders arranged at either or both sides of the penetrating segment. If the penetrating segment and pressing shoulders are fixed to separate press jaws, it is preferably that they press simultaneously. The press jaws, in particular, the penetrating segments can have a straight, sinusoidal, spiral or helical shape in the longitudinal direction to form essentially straight, sinusoidal, spiral, or helical grooves in the axial direction of the tampon. The resultant tampon has at least three ribs, in transverse cross-section, has a median at least partially diverging from the radius where the median of the rib is the line drawn through the midpoint of a series of arc lines, bound by the edges of the rib, wherein the arcs have a common center which is the midpoint of the X-X cross-section of the tampon.

Schmidt, EP 1459720 B1, purports to disclose increasing the surface area of a tampon by utilizing grooves that are formed in a wave shape. While multiple examples are shown, including wavy grooves with angled points, this publication does not disclose specifics on how to manufacture the tampons. In particular, the publication does not include specifics about compression, the press jaws or how the preform or tampon is ejected from the press.

Ruhlmann, WO 2009/129910 A1, purports to disclose a tampon having at least one first surface groove and at least one second surface groove that crosses the first surface groove along their path between a proximal end and a distal end of the tampon. However, the disclosure fails to teach how the crossing grooves are formed, especially in a commercially-feasible manufacturing process and/or with a cover.

Fung, US 2011-0092940 A1, discloses an intravaginal tampon formed of compressed material and has an outer surface with at least two segmented grooves are formed therein, and each segmented groove is separated from and spaced at a distance from an adjacent segmented groove. Each segmented groove has at least one substantially longitudinal segment and at least one accumulator segment. The arrangement of the segments provides a pooling region to impede bodily fluid flow along the outer surface of the tampon.

Kimball et al., U.S. Pat. Nos. 8,834,439, 8,827,975, and 9,168,184 disclose improved tampons having intersecting, penetrating groove segments and processes and apparatus for producing them.

What is needed is an improved tampon press to produce more consistently and cleanly finished tampons having intersecting, penetrating groove segments.

SUMMARY OF THE INVENTION

It has been discovered that a modified set of tampon press jaws provides consistent, cleanly finished tampons having intersecting, penetrating groove segments.

In one aspect of the invention, an apparatus for manufacturing an intravaginal tampon for feminine hygiene includes a tampon press having a plurality of elongate press dies disposed about central press axis to form a press cavity and a cylindrical carrier having a diameter less than that of the predetermined finished diameter. The elongate press dies include a plurality of longitudinal penetrating dies having pressing faces corresponding to a plurality of longitudinal groove segments in a desired compressed tampon pledget and including at least one first penetrating die having a pressing shape corresponding to a desired first groove segment shape and at least one second penetrating die having a pressing face corresponding to a second groove segment shape, wherein the first groove segment shape and the second groove segment shape combine to form a groove form on a tampon. The pressing face of the first penetrating die extends longitudinally beyond the pressing face of the second penetrating die toward an end of the press cavity. The at least one first penetrating die has a pressing face notch disposed proximate a first end thereof and an end notch disposed on an edge perpendicular to the pressing face at the opposite second end thereof, and wherein the at least one second penetrating die has a pressing face notch disposed proximate a second end thereof (corresponding and adjacent to the second end of the at least one first penetrating die) and an end notch disposed on an edge perpendicular to the pressing face at the opposite first end thereof (corresponding and adjacent to the first end of the at least one first penetrating die.

Other aspects and features of the present invention will become apparent in those ordinarily skilled in the art upon review of the following description of specific embodiments of the invention in conjunction with the accompanying drawings.

DETAILED DESCRIPTION OF THE PREFERRED EMBODIMENTS

Figure 1:
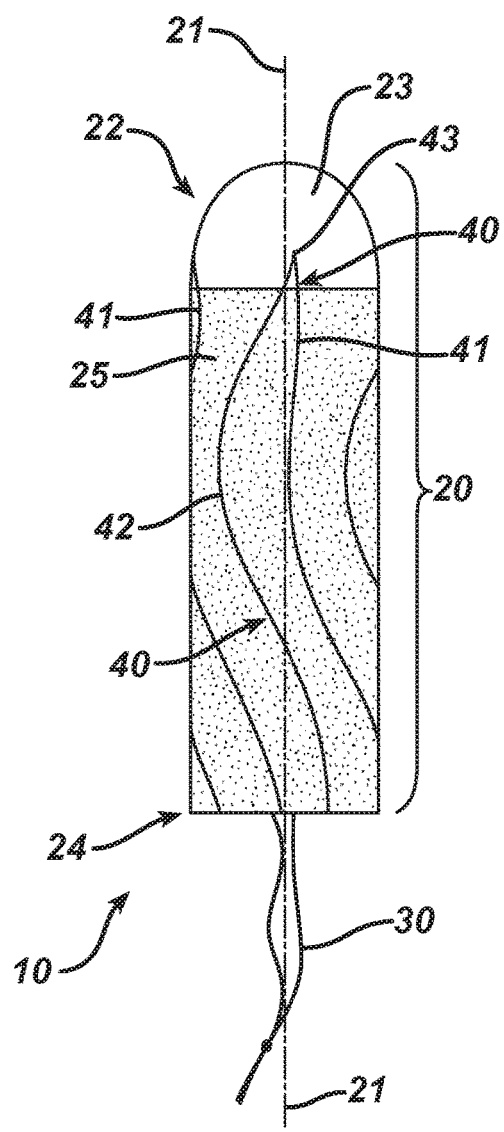
FIG. 1 is a side view of a tampon according to the prior art.

I have learned that the prior art, especially described in Kimball et al., U.S. Pat. Nos. 8,834,439, 8,827,975, and 9,168,184, can form nicely defined intersecting groove forms in a controlled environment, the well-defined groove forms can suffer as tampon diameters change and the process is scaled up to high-speed manufacturing. These changes may result in incomplete intersecting grooves as some of the fibers were not fully "tucked" into the tampon grooves. Therefore, I have developed an improved tampon press to reliably produce cleanly finished tampons having well-defined, intersecting, penetrating groove segments.

As used herein the specification and the claims, the term "groove" and variants thereof relate to an indention into the surface of the tampon. For clarification, grooves may be "penetrating grooves", extending at least 0.7 mm (or 10% of the radius, whichever is greater) into the tampon. Regions between grooves may take the form of ribs.

As used herein the specification and the claims, the term "groove form" and variants thereof relates to a groove or combination of groove segments that are connected in a visibly identifiable manner to provide a unique detached feature at least on the surface of the tampon pledget.

As used herein the specification and the claims, the term "turn" and variants thereof relates to a portion of the groove form in which the groove and/or groove elements reverse(s) upon itself/themselves in a substantially U-shaped or a substantially V-shaped configuration. A "turn" can also have a generally linear extension from the intersection, such as a substantially Y-shaped configuration.

As used herein the specification and the claims, the term "major axis" and variants thereof relating to the groove form is defined by the shortest line connecting the most distant points of the groove form. Generally, this major axis will pass through at least one turn proximate to one end of the pledget.

As used herein the specification and the claims, the term "longitudinal axis" and variants thereof relate to an axis that runs from the insertion end to the withdrawal end substantially through the center of the tampon.

As used in the specification and the claims, the term "self sustaining shape" and variants thereof relate to a tampon pledget that is compressed and/or shaped to assume a general shape and size that is dimensionally stable. For example, a digital tampon that has a self-sustaining shape will generally maintain its shape after a primary package or overwrap is removed and will generally maintain such shape for vaginal insertion. It will be recognized that the tampon is intended to absorb bodily fluids, and may substantially change shape during use as it absorbs such fluids.

As used in the specification and the claims, the term "pledget" and variants thereof relate to a pad or a compress of absorbent material such as fibers designed to absorb bodily fluids.

As used in the specification and the claims, the term "oriented substantially longitudinally" and variants thereof relate to a groove or a groove segment or a groove form that has a helix angle of greater than 45°.

As used in the specification and the claims, the term "fiber density" and variants thereof relate to the relative proportion of fibers to void space in a given volume of the fibrous structure.

The present invention relates to a tampon with reduced opportunity for bodily fluid to flow along the surface without being absorbed into the tampon pledget. This is accomplished by providing at least two detached groove forms each having a generally longitudinal orientation, a length (measured along the groove) that is at least 150% of the length of the pledget, and a turn proximate to at least one of an insertion end and a withdrawal end. The detached groove forms provide visually distinct zones with different bodily fluid handling characteristics. In addition, the turn proximate to at least one end of the tampon provides at least two groove paths for the fluid to follow to be distributed to different portions of the tampon pledget. Thus, not only does the present invention provide tampons with a plurality of grooves, recognized by the prior art as providing improved fluid handling characteristics, but it also provides either fully or partially closed absorption zones that visually communicate functional benefits to the user, including absorbent reservoirs to better contain bodily fluids in the tampon.

Referring to FIG. 1, an intravaginal tampon 10 for feminine hygiene includes a generally cylindrical absorbent pledget 20 and a withdrawal element 30 extending therefrom. The pledget 20 has a longitudinal axis 21, an insertion end 22 (which may terminate in a dome 23), and a withdrawal end 24. The pledget includes a mass of fibers compressed into a self sustaining shape and a sheet-like fluid-permeable cover 25 (such as an apertured film cover) substantially enclosing the mass of fibers. The withdrawal element 30, such as a string, is operatively connected to and extends from the pledget 20 proximate to the withdrawal end 24 thereof.

The pledget 20 includes a plurality of detached groove forms 40 arranged about the outer surface of the pledget 20. In embodiment of FIG. 1, the detached groove forms 40 each comprise a pair of wavy groove segments 41,42 that intersect to create a turn 43 proximate to the insertion end 22 of the pledget 20 and are separate proximate to the withdrawal end 24.

Figure 2:
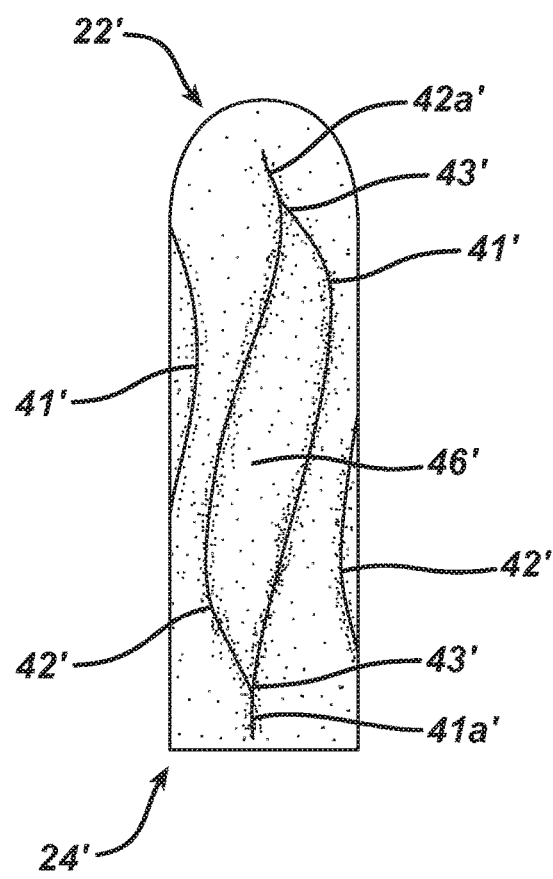
FIG. 2 is a side view of a tampon manufactured with the tampon press jaws according to the present invention.

FIG. 2 shows a tampon manufactured with the press jaws of the present invention. The detached groove forms 40' each comprise a pair of groove segments 41',42' that intersect to create a turn 43' proximate to both the insertion end 22 and the withdrawal end 24 of the pledget 20 to provide discrete surface zones 46 bounded by the encircling groove forms 40'. In addition, a continuation of one detached groove form extends beyond each turn 41a', 42a'.

In the present invention, the groove forms may comprise a plurality of groove segments. These groove segments may have a configuration that is a straight line, a plurality of linked angled segments (such as a saw tooth waveform or a square waveform), a plurality of curved segments (such as a sinusoidal waveform), and combinations thereof.

The configuration of the groove segments may differ between groove forms, or they may be the same. The configuration of groove segments within each groove form may also be the same or different. Additional grooves, including longitudinal grooves 44, may be configured similarly to or distinct from each other and the configuration of the groove segments making up the groove forms 40.

The absorbent pledget includes a mass of fibers compressed into a self sustaining shape. The pledget may also include additional absorbent materials such as foam, super-absorbent, hydrogels, and the like. Preferred absorbent material for the present invention includes foam and fiber. Absorbent foams may include hydrophilic foams, foams which are readily wetted by aqueous fluids as well as foams in which the cell walls that form the foam themselves absorb fluid.

Preferably, the fibers employed in the formation of the absorbent body include regenerated cellulosic fiber, natural fibers and synthetic fibers. Preferably, the materials employed in the formation of a tampon according to the present invention include fiber, foam, hydrogels, wood pulp, superabsorbents, and the like. A useful, non-limiting list of useful absorbent body fibers includes natural fibers such as cotton, wood pulp, jute, and the like; and processed fibers such as regenerated cellulose, cellulose nitrate, cellulose acetate, rayon, polyester, polyvinyl alcohol, polyolefin, polyamine, polyamide, polyacrylonitrile, and the like. Other fibers in addition to the above fibers may be included to add desirable characteristics to the absorbent body. Preferably, tampon fibers are rayon, cotton, or blends thereof, and more preferably, the fibers are rayon. The fibers may have any useful cross-section.

Fiber cross-sections include multi-limbed and non-limbed. Multi-limbed, regenerated cellulosic fibers have been commercially available for a number of years. These fibers are known to possess increased specific absorbency over non-limbed fibers. A commercial example of these fibers is the Galaxy® multilimbed viscose rayon fibers available from Kelheim Fibres GmbH, Kelheim, Germany. These fibers are described in detail in Wilkes et al., U.S. Pat. No. 5,458,835, the disclosure of which is hereby incorporated by reference. Preferably, the fibers include hydrophilic fibers, and more preferably, the fibers include absorbent fibers, i.e., the individual fibers, themselves, absorb fluid. A useful, non-limiting list of useful tampon fibers includes natural fibers such as cotton, wood pulp, jute, hemp, and the like; and processed fibers such as regenerated cellulose, cellulose nitrate, cellulose acetate, rayon, polyester, polyvinyl alcohol, polyolefin, polyamine, polyamide, polyacrylonitrile, and the like. Other fibers in addition to the above fibers may be included to add desirable characteristics to the absorbent body. For example, hydrophobic fibers may be used in outer surfaces of the tampon to reduce surface wetness and hydrophilic fibers may be used to increase the rate of fluid transport into and throughout the body. Preferably, the tampon fibers are rayon or cotton, and more preferably, the fibers are rayon. The fibers may have any useful cross-section.

The pledget includes a mass of fibers substantially enclosed by a sheet-like cover material fluid-permeable cover. Thus, the cover encloses a majority of the outer surface of the tampon. This may be achieved as disclosed in Friese, U.S. Pat. No. 4,816,100, the disclosure of which is herein incorporated by reference. In addition, either or both ends of the tampon may be enclosed by the cover. Of course, for processing or other reasons, some portions of the surface of the tampon may be free of the cover. For example, the insertion end of the tampon and a portion of the cylindrical surface adjacent this end may be exposed, without the cover to allow the tampon to more readily accept fluids.

The cover can ease the insertion of the tampon into the body cavity and can reduce the possibility of fibers being separated from the tampon. Useful covers are known to those of ordinary skill in the art, and they are generally dimensionally stable with low elongation in both the machine and cross-direction. They may be selected from an outer layer of fibers which are fused together (such as by thermobonding), a nonwoven fabric, an apertured film, or the like. Preferably, the cover has a hydrophobic finish.

While liquid permeable covers are beneficial additions to radially-compressed tampons, their dimensional stability can produce some processing challenges. For example, radially compressing a cylindrical tampon blank having a dimensionally stable cover disposed about the cylindrical outer surface can result in cover wrinkles or loose cover extending from the outer surface of the compressed tampon pledget. Therefore, many processes involving radial compression of a tampon blank account for this by folding or tucking the cover material into grooves or folds that penetrate relatively deeply into the absorbent structure.

A process useful in the formation of an intravaginal tampon for feminine hygiene of the present invention with grooved zones begins with an open fibrous structure. The open structure may be a nonwoven fibrous web, a mass of randomly or substantially uniformly oriented fibers and optional materials, such as foams, or particles, and the like. This mass is then manipulated to form a tampon blank.

A nonwoven web useful in the present invention can be formed in any manner desired by the person of ordinary skill in the art. For example, fibers can be opened and/or blended by continuously metering them into a saw-tooth opener. The blended fibers can be transported, e.g., by air through a conduit to a carding station to form a fibrous web. Alternatively, a mass of substantially randomly oriented fibers can be formed by opening and/or blending them, transporting them, as above, to a station to form, e.g., a teabag-type tampon blank. Further processes may employ oriented fibers in a fibrous tow.

The tampon blank can be further processed to form a tampon. In a tampon forming process, a web can be formed into a narrow, fibrous sliver and convolutely wound to form a tampon blank. In addition, a liquid-permeable cover material can be wrapped around the tampon blank to substantially contain the fibrous absorbent portion of the tampon. It may be desired to process the fibrous sliver with selective needle-punching of the sliver as disclosed in U.S. Pat. No. 7,845,055 to Kimball et al., the disclosure of which is herein incorporated by reference.

Figure 3:
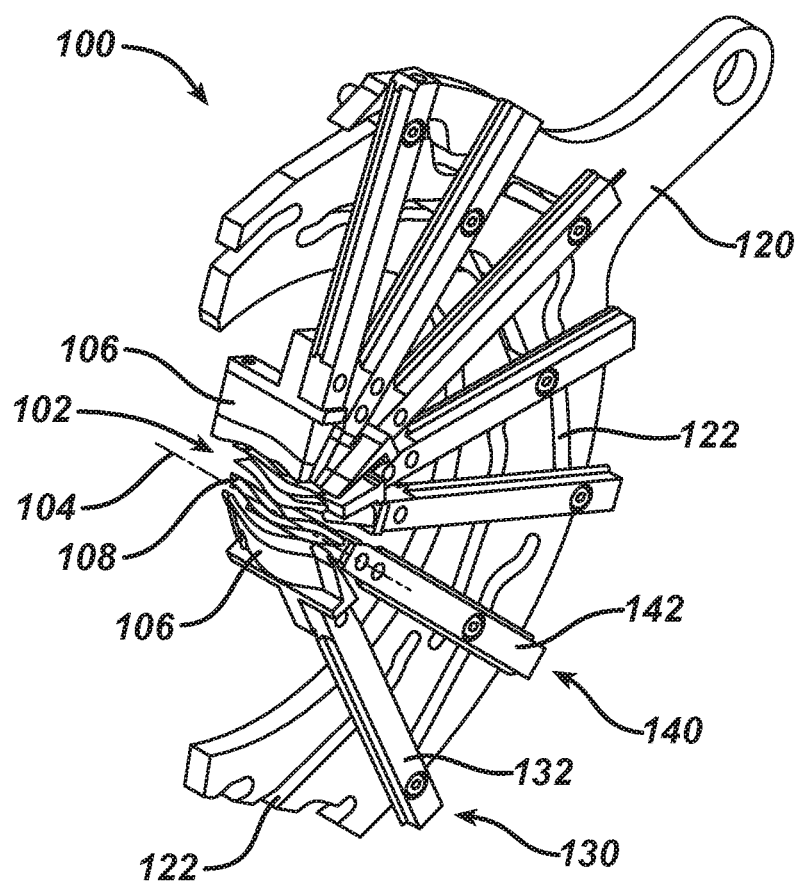
FIG. 3 is a perspective view of a press having a single cam useful in forming tampons of the present invention; the cam is partially broken away, and some of the press elements have been removed for increased clarity of the illustrated press elements.

As shown in FIGS. 3-12, the intravaginal tampon for feminine hygiene of FIG. 1 having a predetermined finished diameter can be formed in a press 100 having (1) a generally cylindrical press cavity 102 having a central press axis 104 and a substantially cylindrical circumference and (2) a plurality of elongate press dies. A partially broken-away perspective view of the press 100 is shown in FIG. 3. This figure includes only seven of sixteen press dies and a portion of the press cam removed for clarity. The press dies may include penetrating dies 106 having pressing faces for defining a set of penetrating grooves that extend into the finished tampon pledget and shaping dies 108 for forming surface features, including shallow grooves on the outer surface of a resulting compressed tampon pledget, or smoothing the outer surface of a resulting compressed tampon pledget, or forming a continuous diameter for guiding resulting compressed tampon pledget out of the press during the ejection step. The penetrating dies 106 and shaping dies 108 alternate about the circumference of the cylindrical press cavity.

Figure 4:
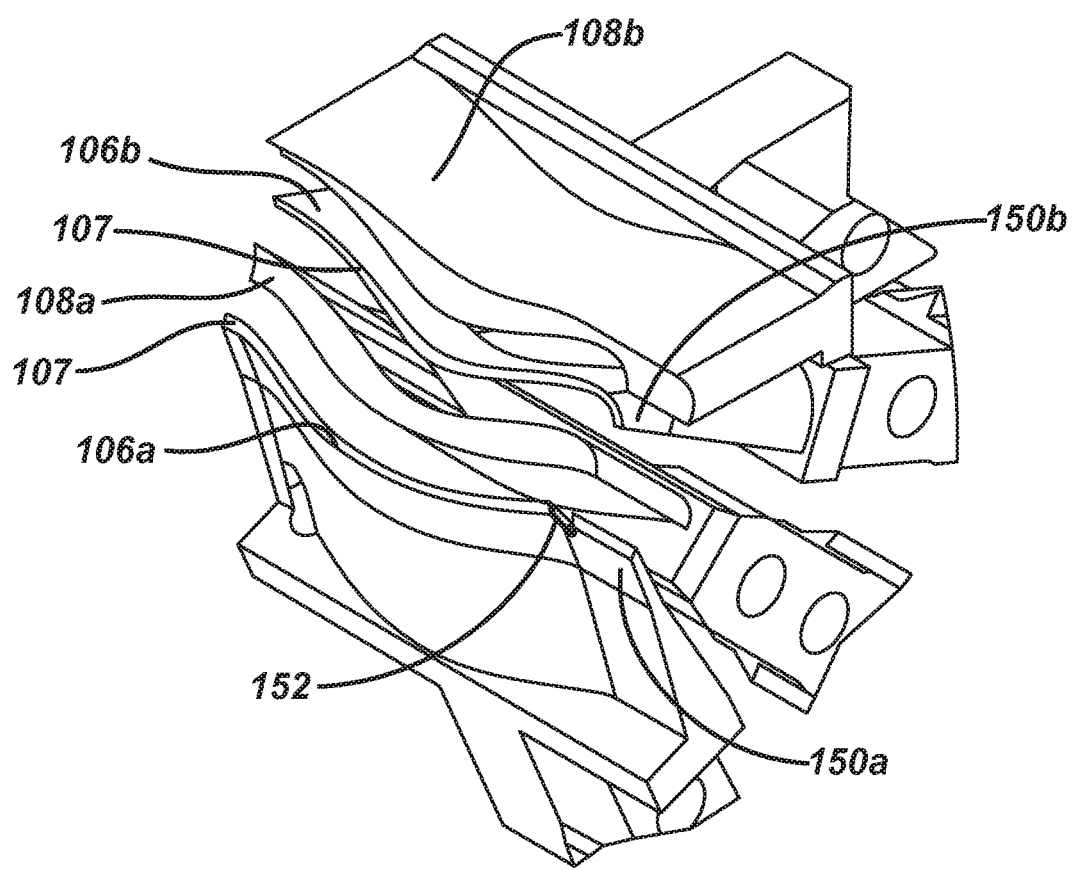
FIG. 4 is perspective view of four of the press dies of the press of FIG. 3.

More detail of the press dies can be seen in FIG. 4, an enlarged view of the bottom right four press dies of FIG. 3. In this view, a first penetrating die 106a has a pressing face 107 and shape corresponding to groove segment 41 and a second penetrating die 106b has a shape corresponding to groove segment 42 (of FIG. 1). As can be seen in FIG. 4, one end 150a of the first penetrating die 106a extends beyond the corresponding end 150b of the second penetrating die 106b. Indeed, the end 150b of the second penetrating die 106b is curved toward the first penetrating die 106a in order to form the turn 43 in the surface of the tampon pledget 20 (as shown in FIG. 1) proximate to the insertion end 22. In this embodiment, the end 150a of the first penetrating die 106a corresponds to the insertion end 22 of the tampon pledget 20 of FIG. 1.

Turn 43 of the detached groove form 40 is formed by the intersection between groove segments 41 and 42 (see FIG. 1). To form a groove form 40, the penetrating dies 106a, 106b travel on a path that crosses during the compression of the tampon blank 200 (see FIG. 5) to form the pledget 20. Therefore, the longer penetrating die 106a has a notch 152 formed (see FIG. 4) proximate to, although spaced from, the end 150a to permit the end 150b of penetrating die 106b to pass across the path of travel of penetrating die 106a.

The shaping dies 108 are shaped to accommodate the shape of the penetrating dies 106 disposed therebetween. Thus, shaping die 108a corresponds to the surface of the pledget 20 contained by the groove segments 41 and 42 and the turn 43. This shaping die 108a is shorter than shaping die 108b corresponds to the surface of the pledget 20 that is open to the insertion end 22.

In the foregoing description, the grouping of the four press pieces may be repeated four times to provide four "petals" around the circumference of the tampon pledget. Alternatively, there could be three sets of the four press dies to form three "petals" around the circumference of the tampon pledget.

Figure 3A:
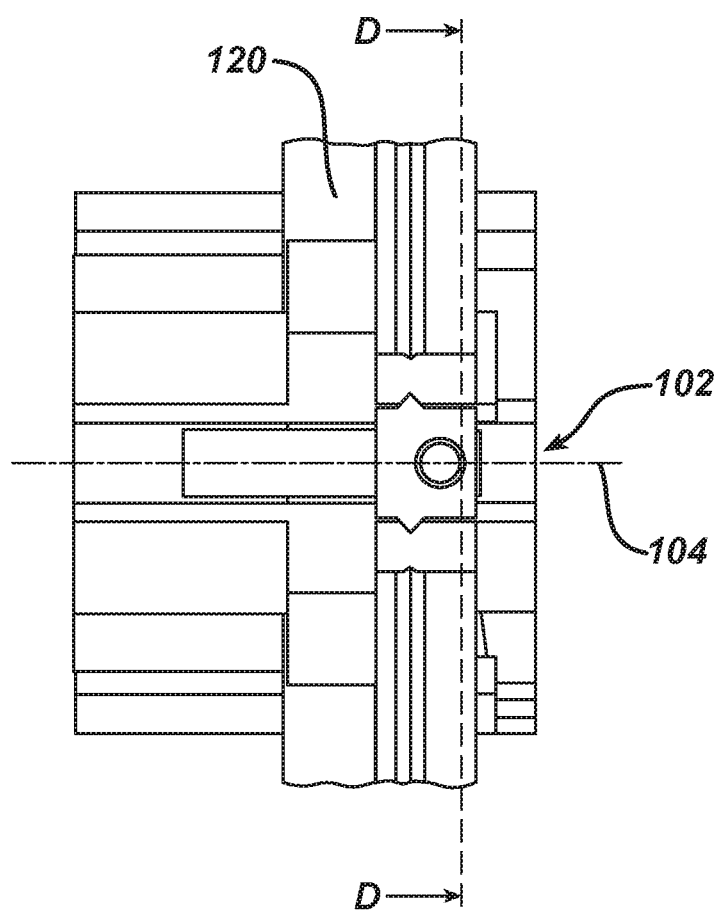
FIG. 3A is a side view of the central portion of the press of FIG. 3 including the press dies and central cavity; outer portions of the cam and other press elements are broken away for increased clarity of the central press portion.
Figure 5:
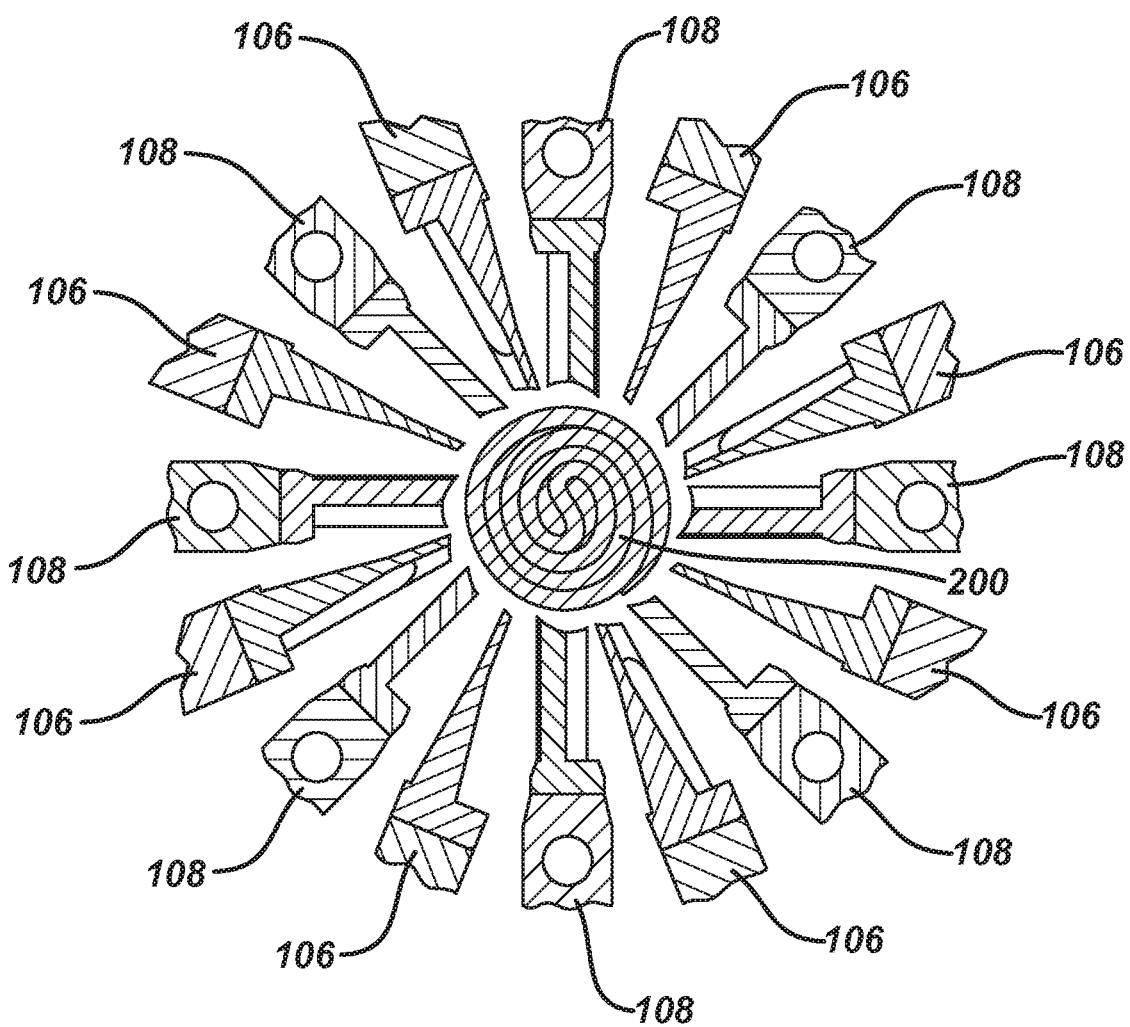
FIG. 5 is cross-section of the central portion of the press of FIG. 3A along line (D-D) in an open position; outer portions of the press elements are broken away for increased clarity of the central press portion.
Figure 6:
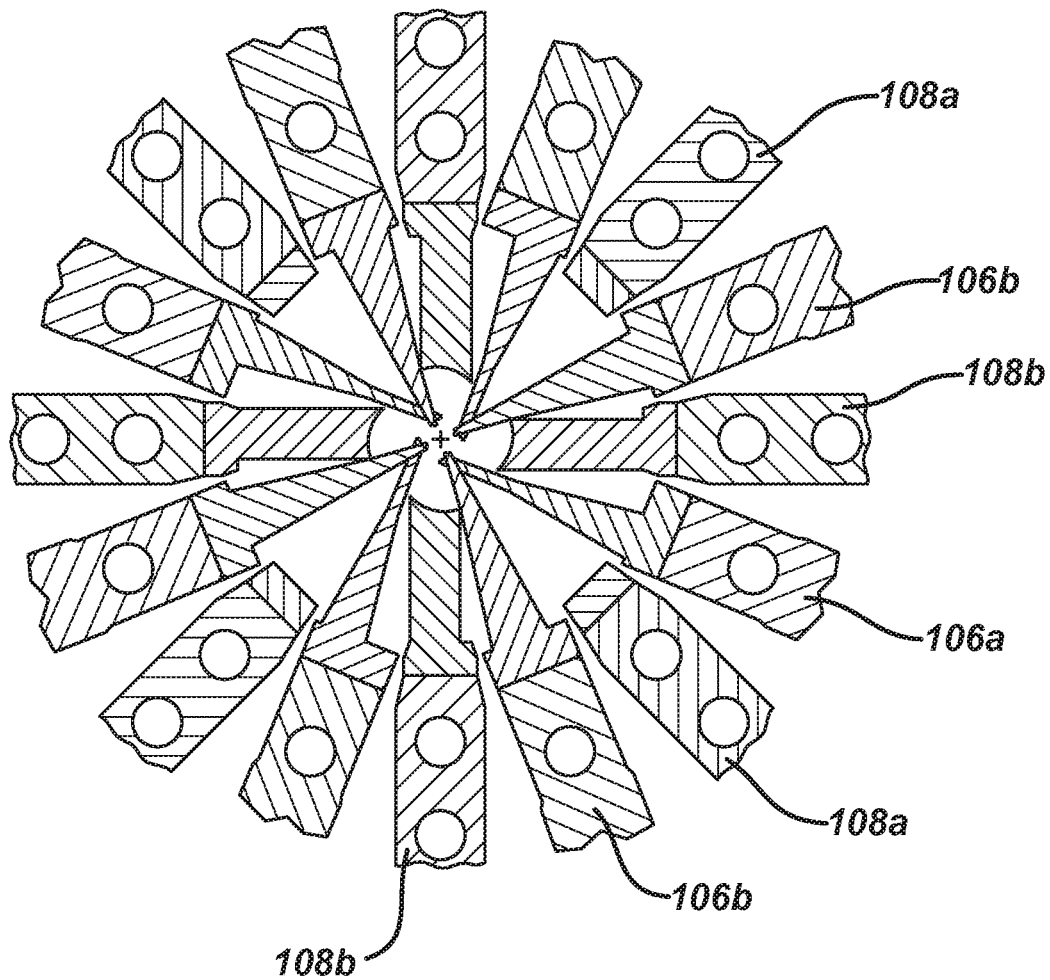
FIG. 6 is cross-section of the central portion of the press of FIG. 3A along line (D-D) during an initial compression step; outer portions of the press elements are broken away for increased clarity of the central press portion.
Figure 7:
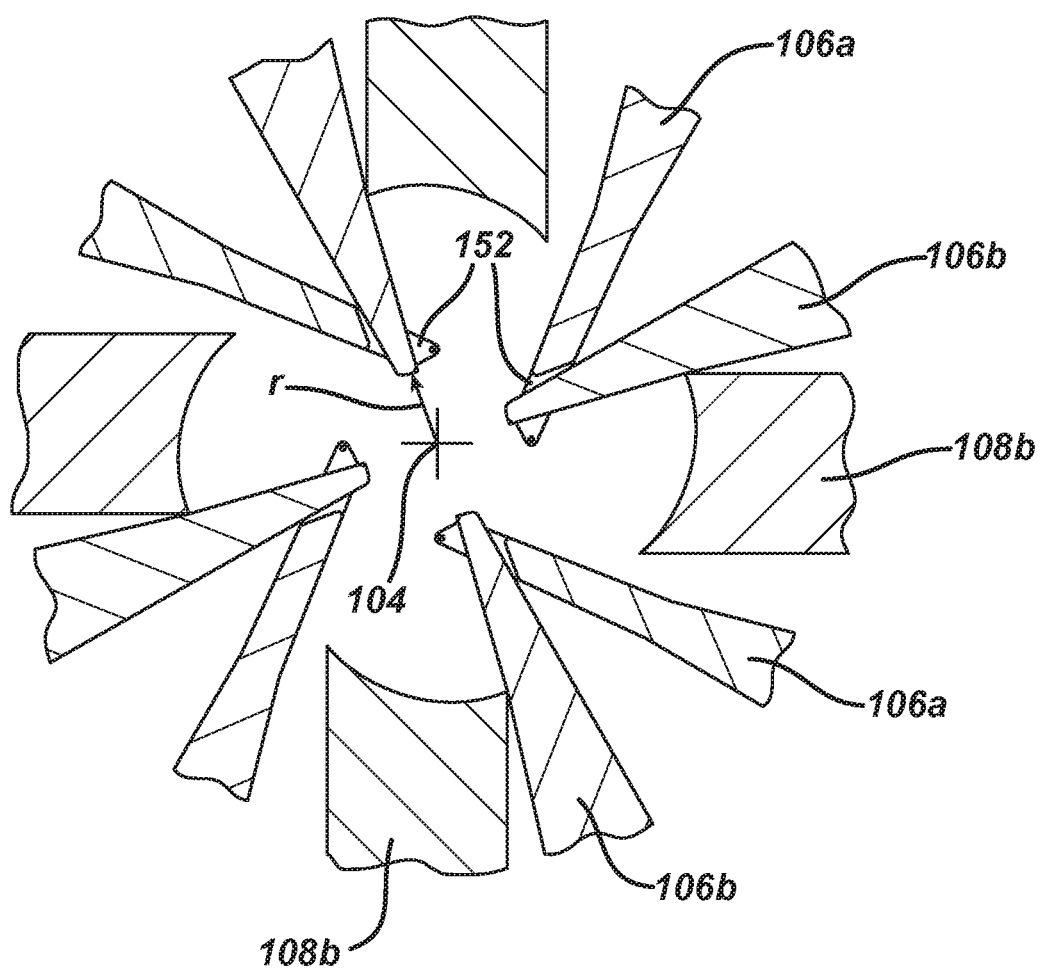
FIG. 7 is an enlarged cross-section view of the press of FIG. 6 clearly showing the penetrating die tips crossing during an initial compression step; the remaining press elements are broken away.
Figure 8:
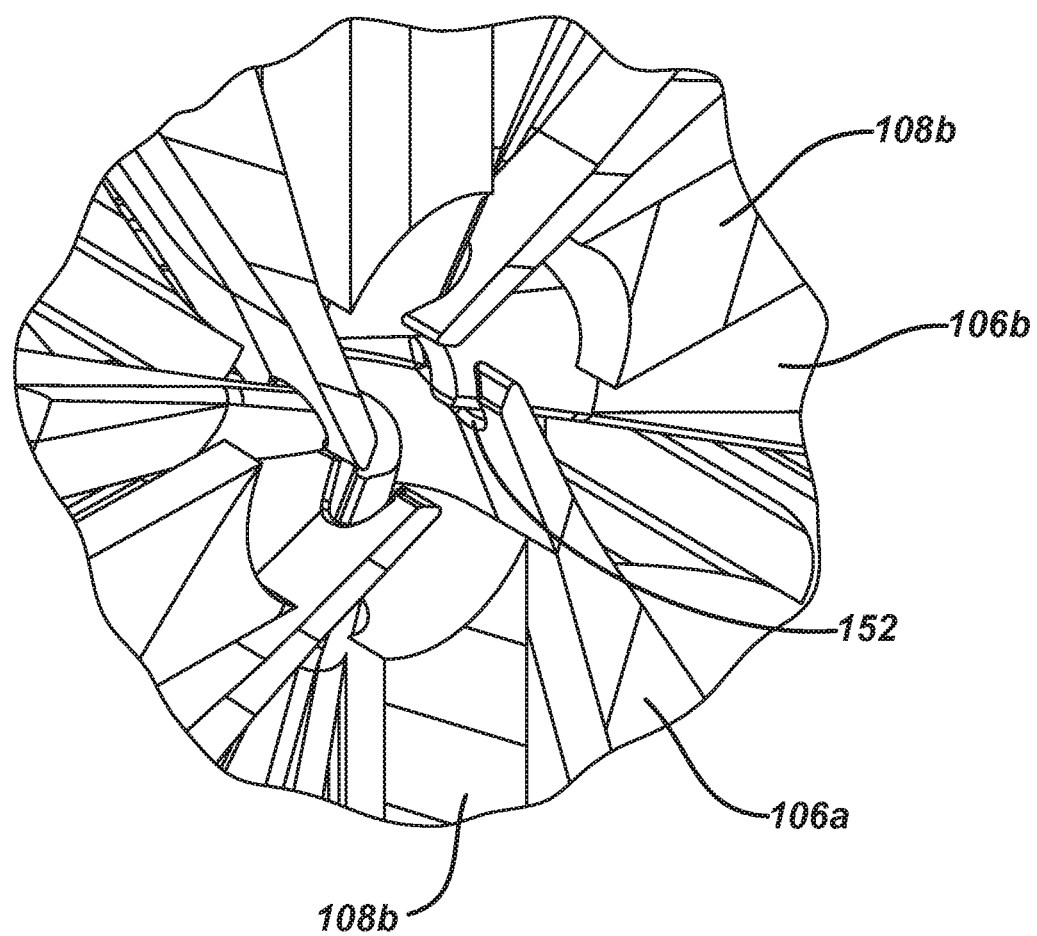
FIG. 8 is an enlarged perspective view of the press of FIG. 7; the remaining press elements are broken away.

In this process, a substantially cylindrical tampon blank 200 is inserted into the press cavity 102 in an open position shown in FIG. 5 (a cross-section of the press of FIG. 3A and tampon proximate to the notch 152 in the first penetrating die 106a, looking from the interior of the press toward the end of the press corresponding to the insertion end of the tampon in FIG. 1), after which an initial compression step is performed. In this initial compression step, at least the penetrating dies 106 are moved into the press cavity 102 to a penetrating die closed position having a clear distance "r" (see FIG. 7) from the press axis 104 that is less than the predetermined finished diameter as shown in FIG. 6 and in detail in FIGS. 7 and 8. This causes portions of adjacent penetrating dies that form the turn to pass through the same space within the press. As shown in FIG. 8, this can be accomplished by forming a notch 152 in the first penetrating dies 106a to permit the second penetrating dies 106b to cross therethrough in the penetrating die closed position. This initial compression step forms the compressed fibrous core of the tampon and provides column strength for easy insertion without need for a tampon applicator, known in the art as digital insertion.

Figure 9:
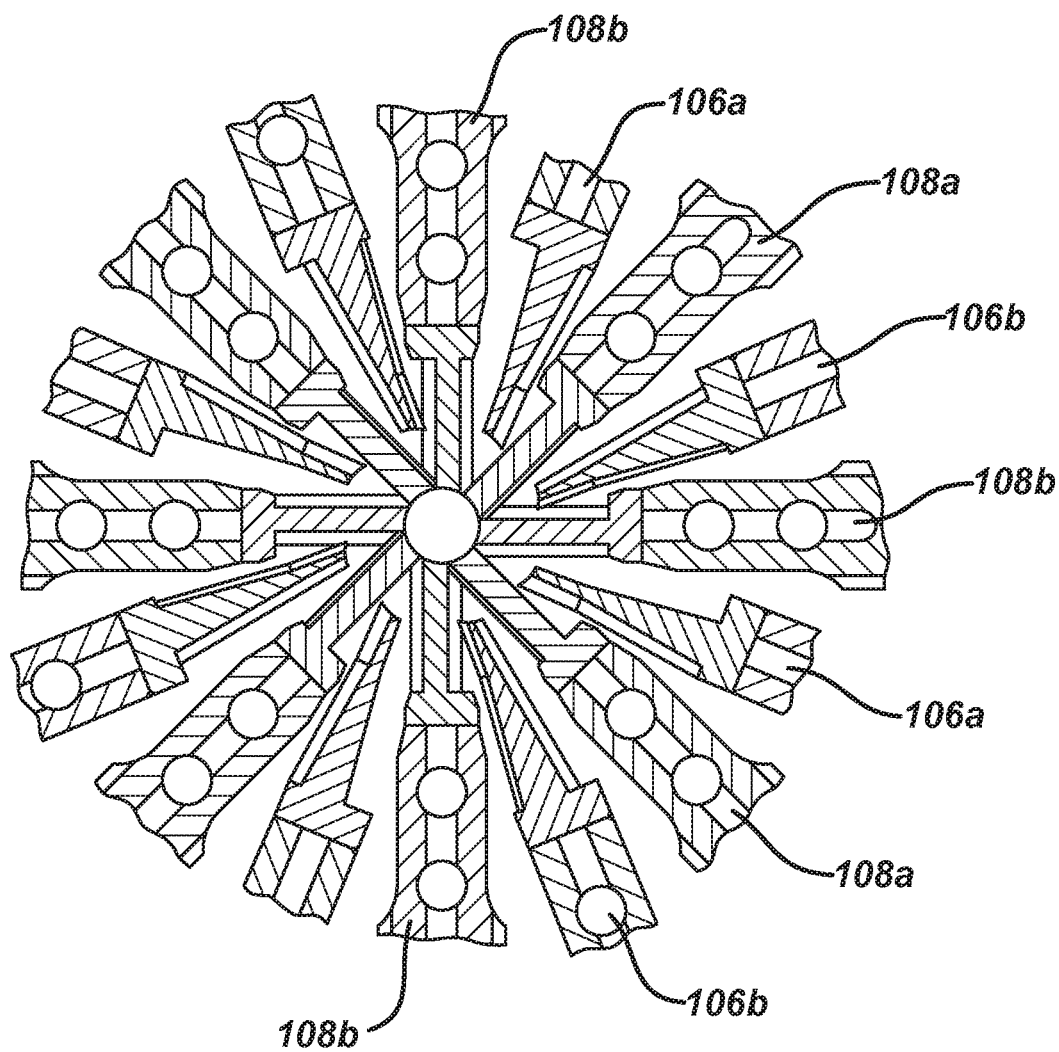
FIG. 9 is cross-section view of the central portion of the press of FIG. 3A along line (D-D) during an ejection step; outer portions of the press elements are broken away for increased clarity of the central press portion.
Figure 10:
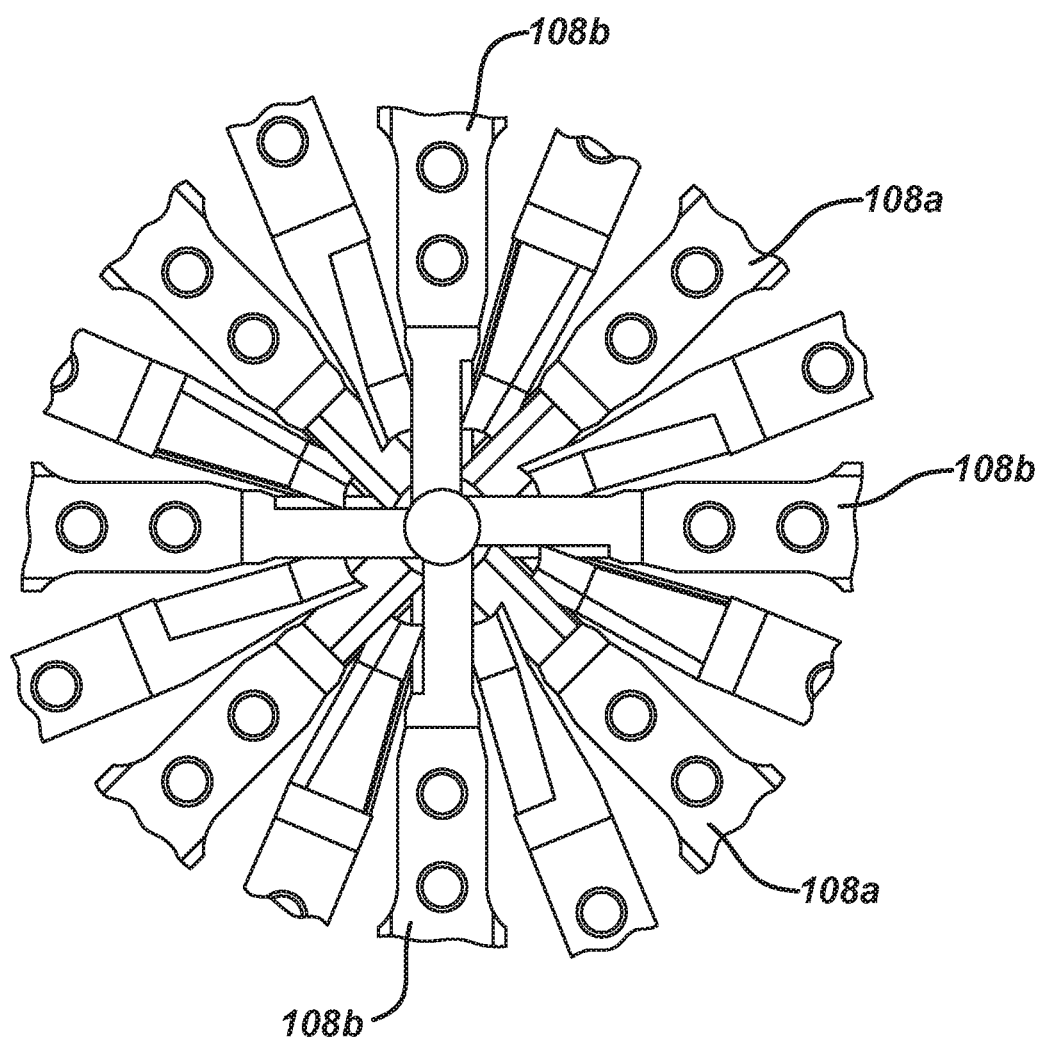
FIG. 10 is an enlarged end view of the press of FIG. 9 in the ejection position.
Figure 11:
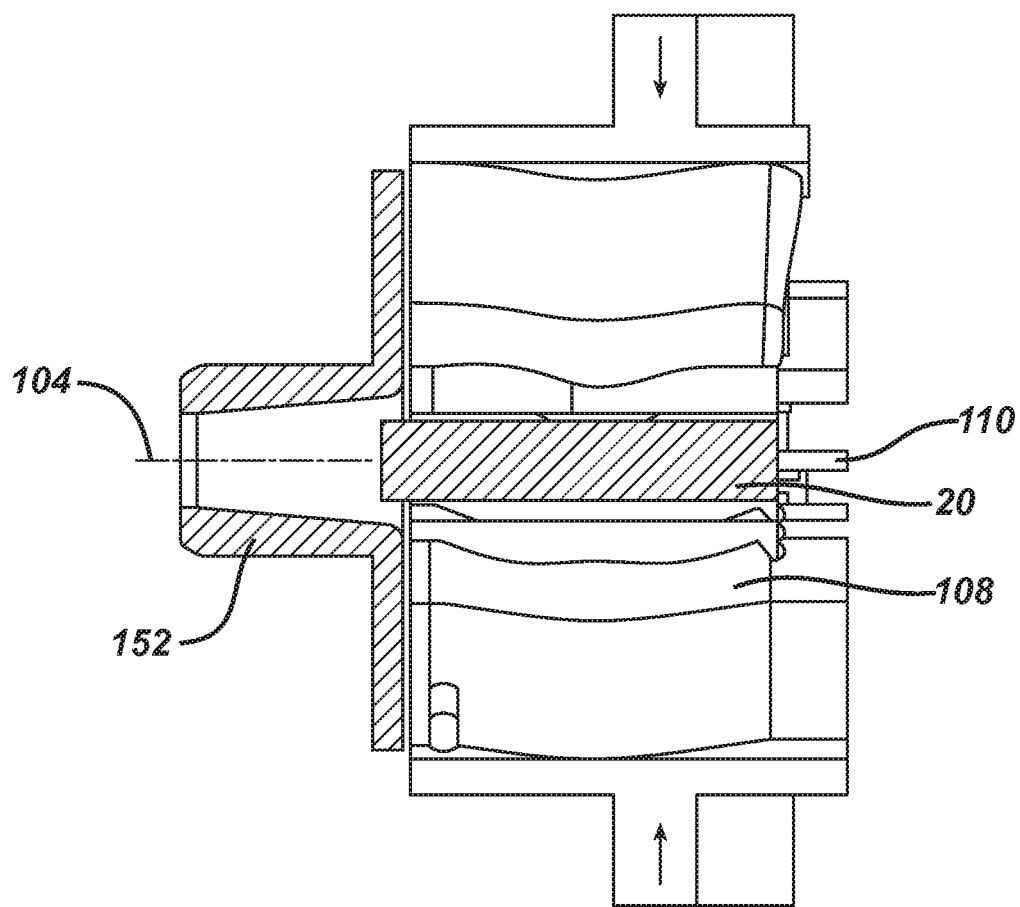
FIG. 11 is a longitudinal cross-section of the press of FIG. 9, during an ejection step.

In one embodiment, a second compression step that applies to the substantially longitudinal ribs of the preform a radial pressure directed toward the central press axis to provide a compressed tampon pledget of reduced diameter relative to the preform is represented in FIGS. 9 (a cross-section of the press, proximate to the center of the press cavity) and 10 (an end view of the press). In this step, the penetrating dies 106 are retracted to assume a clear distance from the press axis that is sufficient to permit the shaping dies 108 to advance toward the press axis beyond the penetrating dies. Then the set of shaping dies is moved to a shaping die closed position. The compressed tampon pledget may be ejected from the press cavity 102 using the shaping dies 108 to provide a substantially smooth guide for the compressed tampon pledget to permit removal of the compressed tampon pledget from the press and pushing on one end of the compressed tampon pledget with a push rod 110 (shown in FIG. 11).

The tampon can be further shaped and packaged. For example, the insertion end can be formed into a hemispherical or elliptical dome shape, and the tampon can be enclosed in a primary packaging material that can also support the final shape of the tampon.

In somewhat greater detail, the tampon press 100 of FIGS. 3 and 4 includes a cam 120, penetrating die assemblies 130, and shaping die assemblies 140. The cam 120 is generally circular and includes slots 122 to urge the die assemblies 130, 140 into and out of the press cavity 102 as the cam is pivoted about the press axis 104. Each penetrating die assembly 130 includes a pair of slides (an exemplary slide 132 is shown on one side of the cam 120; another, not shown, would be on the opposite side of the cam 120) and the penetrating die 106. Each shaping die assembly 140 includes a pair of slides (an exemplary slide 142 is shown on one side of the cam 120; another, not shown, would be on the opposite side of the cam 120) and the shaping die 108. Alternatively, multiple cams 120a, 120b may be used to permit more variability to the control of the movement of the dies, e.g., one cam could operate penetrating dies 106 and another could operate shaping dies.

Figure 12:
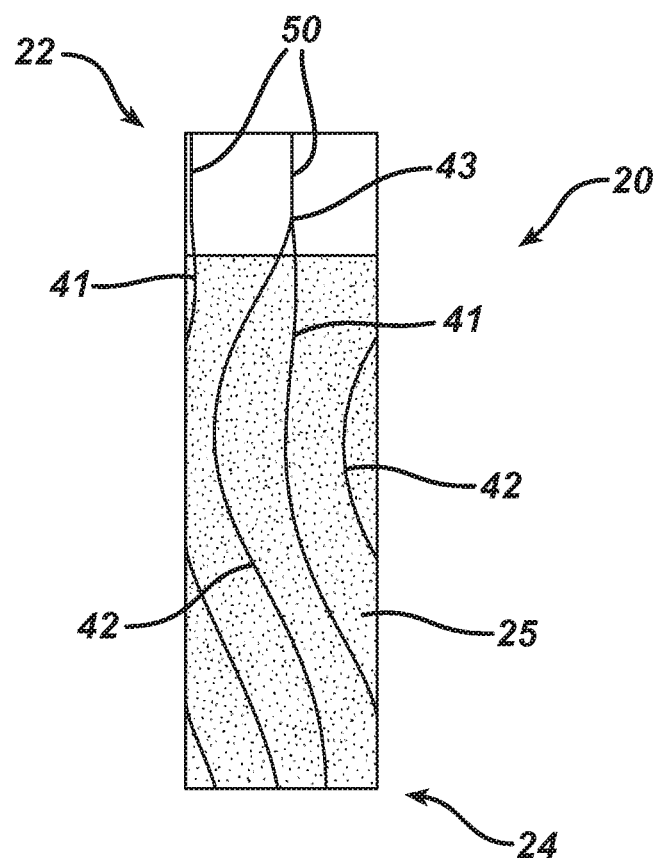
FIG. 12 is a side elevation of a compressed tampon pledget prior to finishing the insertion end and packaging.

Upon ejection from the press 100, compressed pledget 20 is generally cylindrical as shown in FIG. 12. The pressed groove segments generally extend from the insertion end 22 to the withdrawal end 24. Those pressed groove segments 50 that extend from the turn 43 to the insertion end 22 of the pledget will essentially be restructured in the doming process mentioned above to substantially eliminate them, both aesthetically and functionally. This is enhanced by the absence of the cover 25 in the region of the dome 23.

In an alternative embodiment, especially enabled by a multiple cam controlled process, the penetrating jaws 106a, 106b may be controlled to advance them separately. For example, penetrating jaw 106b may be advanced to the closed position, withdrawn sufficiently to permit penetrating jaw 106a to fully advance toward the press axis 104 in the closed position. This eliminates the need for notch 152 in penetrating jaw 106a, as the two penetrating jaws do not need to occupy the same space at the same time. In addition, as described in the embodiment, below, this could permit penetrating jaws 106a to remain in contact with the compressed tampon pledget 20 during ejection from the press.

While the foregoing detailed embodiments describe tampons having four groove forms resulting from eight intersecting groove segments, it will be recognized that the number of groove forms and/or groove segments can be varied, as desired. There may be an even or odd number of groove forms and/or groove segments. A corresponding number of penetrating dies would be required in contrast with the sixteen penetrating dies described in reference to FIGS. 3-12, above.

In the tampon press of the present invention, the press dies of FIGS. 4-11 are revised as described below.

Figure 13:
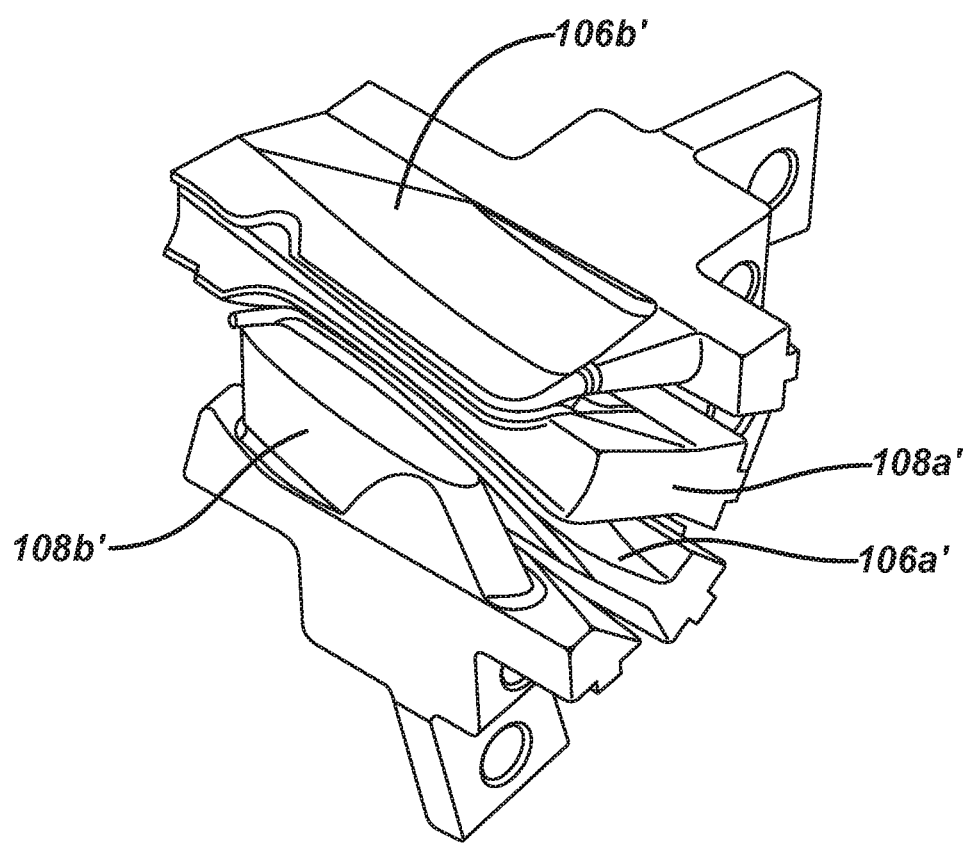
FIG. 13 is a perspective view of four of the press dies of the tampon press of the present invention, similar to the view shown in FIG. 4.

The penetrating dies 106' are formed in pairs, a first penetrating die 106a' has a pressing face 107' and shape corresponding to groove segment 41' and a second penetrating die 106b' has a shape corresponding to groove segment 42' (of FIG. 2). Similar to the penetrating dies of FIG. 4, FIG. 13 shows that one end 150a' of the first penetrating die 106a' extends beyond the corresponding end 150b' of the second penetrating die 106b'. Indeed, the end 150b' of the second penetrating die 106b' is curved toward the first penetrating die 106a' in order to form the turn 43' in the surface of the tampon pledget 20' (as shown in FIG. 2) proximate to the insertion end 22'. In this embodiment, the end 150a' of the first penetrating die 106a' corresponds to the insertion end 22' of the tampon pledget 20' of FIG. 2. In addition, the opposite end 150b" of the second penetrating die 106b' extends beyond the corresponding end 150a" of the first penetrating die 106a'. It is also curved to form the turn 43' proximate the base 24' of the tampon pledge 20'.

Figure 14:
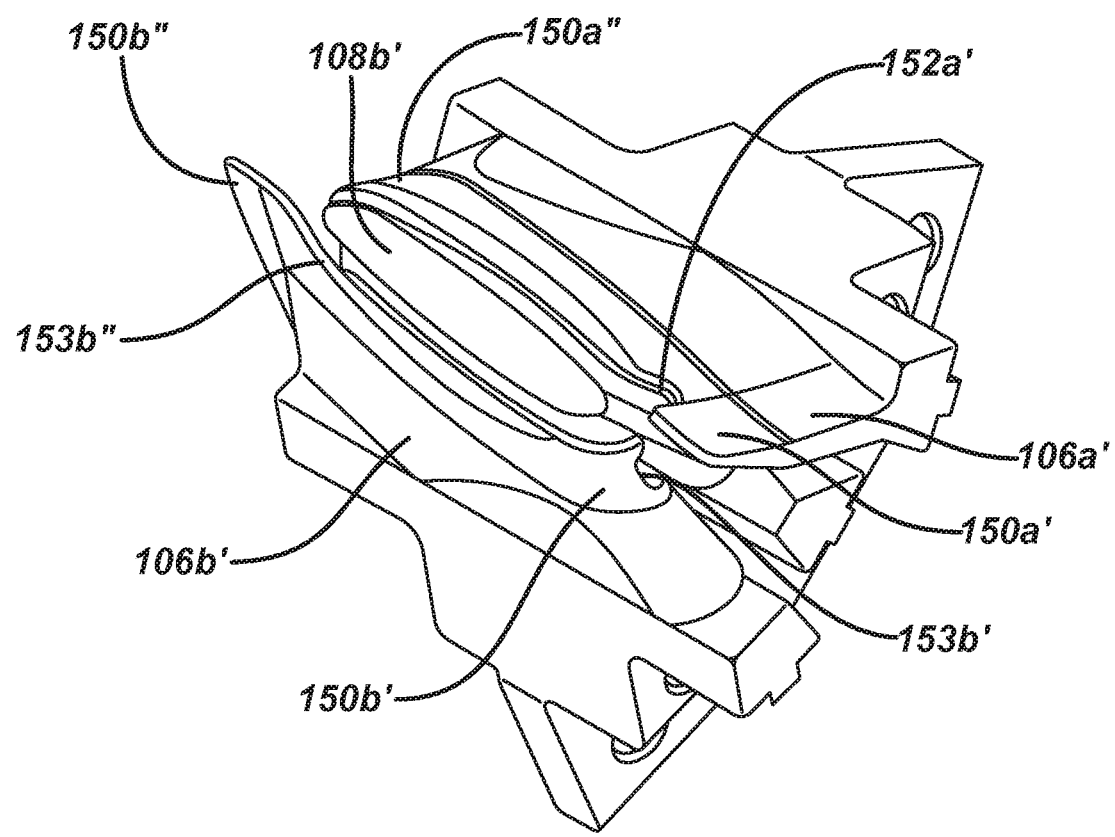
FIG. 14 is a perspective view of three of the press dies of the tampon press of the present invention, including two penetrating dies and an intermediate shaping die, that together form a pair of penetrating groove segments that define a discrete surface zone.
Figure 15:
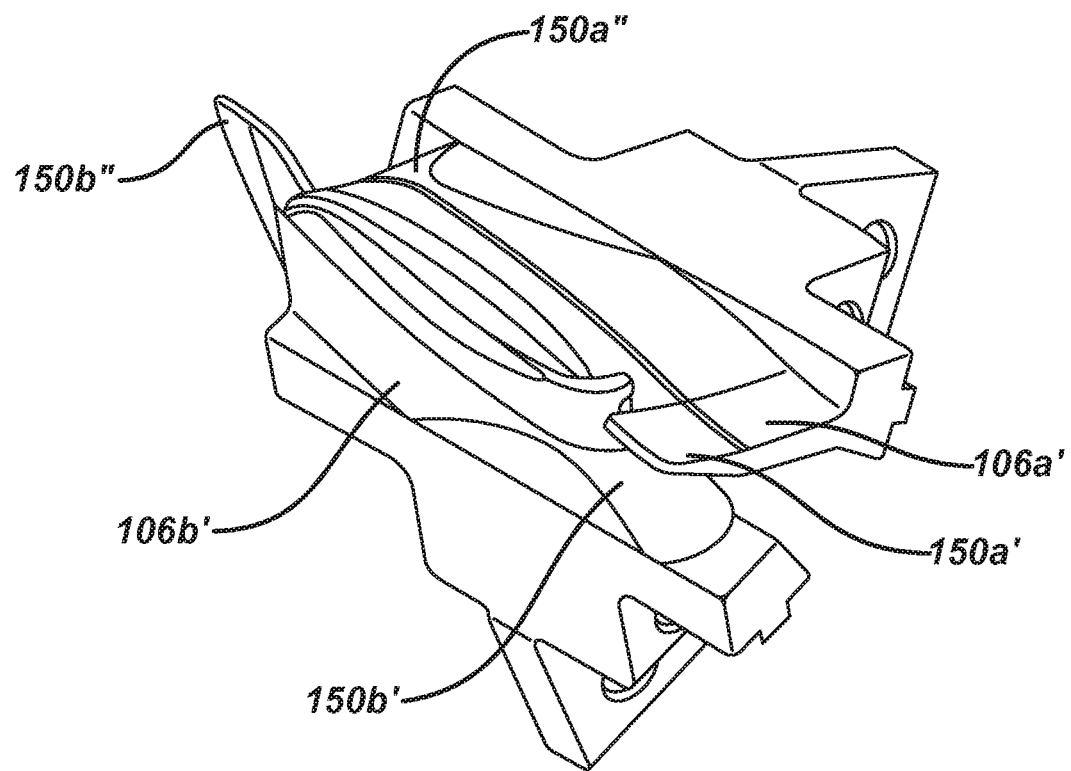
FIG. 15 is a perspective view of the two penetrating dies of FIG. 14 in a fully extended position, illustrating the engagement of the pressing face and end notches.

Again, turn 43' of the detached groove form 40' is formed by the intersection between groove segments 41' and 42' (see FIG. 2). To form a groove form 40', the penetrating dies 106a',106b' travel on a path that crosses during the compression of the tampon blank (similar to that shown in FIG. 6 for the prior art) to form the pledget. Therefore, penetrating die 106a' has a pressing face notch 152a' formed (see FIGS. 13-15) proximate to, although spaced from, the end 150a' to permit the end 150b' of penetrating die 106b' to pass across the path of travel of penetrating die 106a'. In addition, penetrating die 106b' has an end notch 153b' that matches with a corresponding pressing face notch 152a' as shown in FIG. 14 and in greater detail in FIG. 15. This arrangement is repeated at the other ends 150a" and 150b" of the penetrating dies 106a' and 106b'.

Again, shaping dies 108' are shaped to accommodate the shape of the penetrating dies 106' disposed therebetween. Thus, shaping die 108a' corresponds to the surface of the pledget 20 outside of the groove segments 41' and 42' and the turns 43' in the tampon of FIG. 2. This shaping die 108a' is longer than shaping die 108b' that corresponds to the surface of the pledget 20 contained by the groove segments 41' and 42' and the turns 43' in the tampon of FIG. 2.

Figure 16:
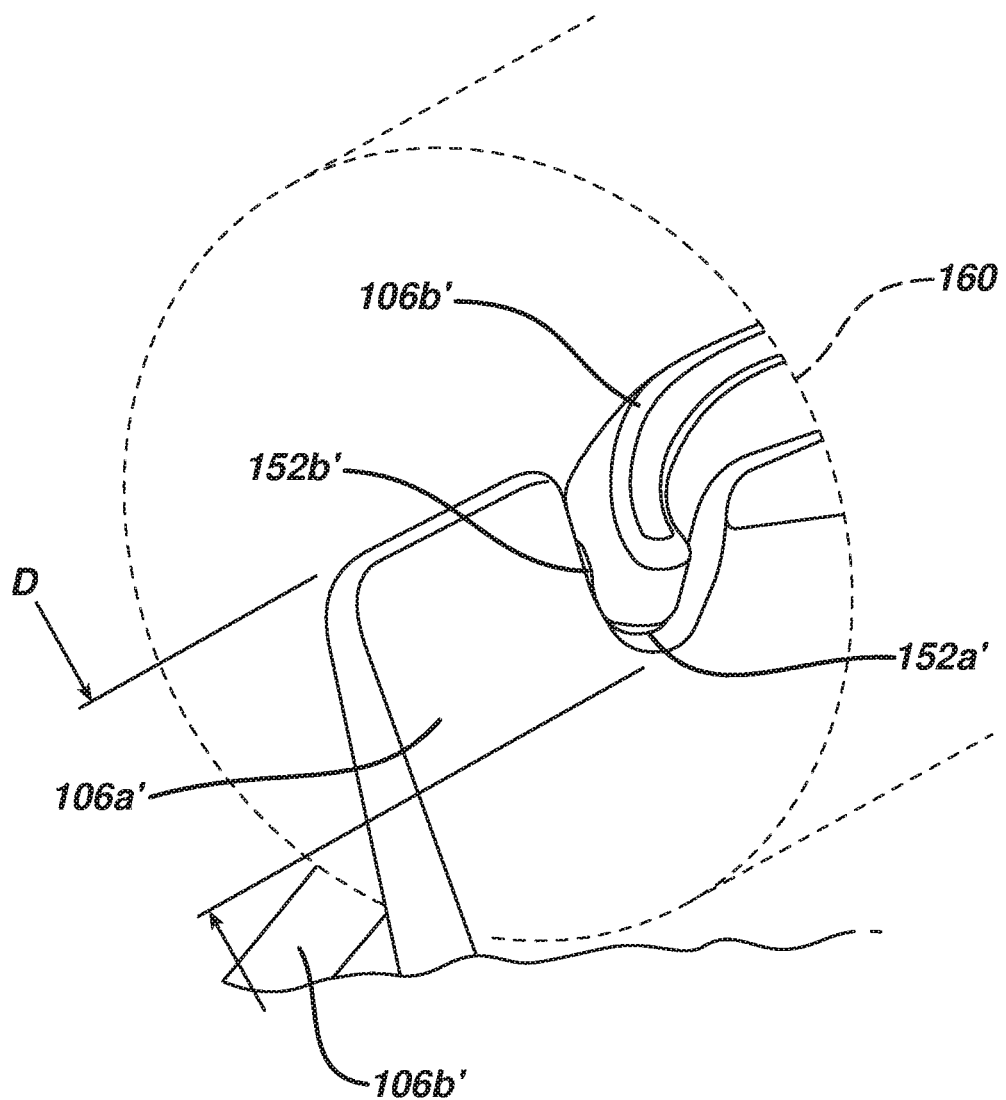
FIG. 16 is schematic view of the interaction of a pressing face notch and an end notch in the context of the dimensions of the finished tampon.

As shown in FIG. 16, the addition of the end notches allows the depth "D" of the pressing face notches 152' to enable all of the pressing face of the penetrating dies 106 to penetrate deeply (at least 3 mm) into the finished tampon diameter. This permits the adjacent penetrating dies to fully "tuck" the fibrous material of the tampon blank below the outer surface 160 of the finished tampon.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. Apparatus for manufacturing an intravaginal tampon for feminine hygiene comprising:
 a) a tampon press having a central press axis comprising:
  i) a plurality of elongate press dies disposed about the central press axis to form a press cavity, the elongate press dies comprising a plurality of longitudinal penetrating dies having pressing faces corresponding to a plurality of longitudinal groove segments in a desired compressed tampon pledget and including at least one first penetrating die having a pressing shape corresponding to a desired first groove segment shape and at least one second penetrating die having a pressing face corresponding to a second groove segment shape, wherein the first groove segment shape and the second groove segment shape combine to form a groove form on a tampon formed in the press, the pressing face of the first penetrating die extends longitudinally beyond the pressing face of the second penetrating die toward an end of the of the press cavity:
   A) wherein the at least one first penetrating die has a pressing face notch disposed proximate a first end thereof and an end notch disposed on an edge perpendicular to the pressing face at the opposite second end thereof, and wherein the at least one second penetrating die has a pressing face notch disposed proximate a second end thereof, corresponding and adjacent to the second end of the at least one first penetrating die, and an end notch disposed on an edge perpendicular to the pressing face at the opposite first end thereof, corresponding and adjacent to the first end of the at least one first penetrating die; and
   B) whereby the first and second penetrating die are capable of passing through the same space within the press to form the groove form; and
  ii. a control mechanism to control movement of the elongate press dies into and out of the press cavity; and
 b. a cylindrical carrier having a diameter less than that of a tampon diameter.

2. Apparatus of claim 1, wherein the plurality of longitudinal penetrating dies comprises at least two pairs of the first and second penetrating dies.

3. Apparatus of claim 1, further comprising a forming die having an exit orifice diameter less than the predetermined finished diameter, the forming die disposed coaxial with the press cavity and adjacent an ejection opening in the press.

4. Apparatus of claim 1 further comprising means to finish one end of the compressed tampon pledget.

5. The apparatus of claim 1, wherein the first and second penetrating dies are arranged and configured to move sequentially within the press and the second penetrating die moves into and withdraws from its position of maximum penetration within the press prior to the first penetrating die moving into its position of maximum penetration within the press.

* * * * *